US008792997B2

(12) United States Patent
Tockman et al.

(10) Patent No.: US 8,792,997 B2
(45) Date of Patent: *Jul. 29, 2014

(54) PEEL-AWAY IS-4/DF-4 LEAD IMPLANT TOOL WITH ELECTRICAL CONTACTS

(71) Applicant: Cardiac Pacemakers, Inc., St. Paul, MN (US)

(72) Inventors: Bruce A. Tockman, Scandia, MN (US); Timothy R. Jackson, Minneapolis, MN (US); Peter J. Wolf, Dresser, WI (US); Christopher A. Fuhs, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/157,286

(22) Filed: Jan. 16, 2014

(65) Prior Publication Data
US 2014/0135884 A1 May 15, 2014

Related U.S. Application Data

(63) Continuation of application No. 13/253,336, filed on Oct. 5, 2011, now Pat. No. 8,666,514.

(60) Provisional application No. 61/415,555, filed on Nov. 19, 2010.

(51) Int. Cl.
*A61N 1/05* (2006.01)
(52) U.S. Cl.
USPC .......................... 607/122; 607/119; 607/126
(58) Field of Classification Search
USPC ......................... 607/119, 122, 126
See application file for complete search history.

(56) References Cited

U.S. PATENT DOCUMENTS

| 4,166,469 A * | 9/1979 | Littleford ...................... 607/122 |
| 4,744,370 A | 5/1988 | Harris |
| 6,038,479 A | 3/2000 | Werner et al. |
| 7,013,182 B1 | 3/2006 | Krishnan |

(Continued)

FOREIGN PATENT DOCUMENTS

| EP | 2111258 | 7/2008 |
| WO | WO2004101068 A1 | 11/2004 |
| WO | WO2005082451 A1 | 9/2005 |

OTHER PUBLICATIONS

International Search Report and Written Opinion issued in PCT/US2011/054887, mailed Dec. 27, 2011, 13 pages.

*Primary Examiner* — Christopher D Koharski
*Assistant Examiner* — Michael Carey
(74) *Attorney, Agent, or Firm* — Faegre Baker Daniels LLP

(57) ABSTRACT

A peel-away lead implant tool is described. The peel away lead implant tool is adapted to be disposed over the terminal connector of a lead during an implantation procedure to protect the terminal connector. The peel-away lead implant tool includes a flexible polymer sheath including electrical contacts formed in a contact region of the sheath. The electrical contacts can be either metal foil contacts or conductive polymer contacts and extend from an outer surface to an inner surface of the sheath such that when the testing apparatus is coupled to the lead implant tool, the electrical contacts are pressed into electrical contact with the ring electrodes located on the terminal connector. The lead implant tool also includes various removal means facilitating the easy removal of the implant tool from the terminal connector when the implantation procedure is complete.

20 Claims, 6 Drawing Sheets

(56) References Cited

U.S. PATENT DOCUMENTS

| | | | |
|---|---|---|---|
| 7,130,699 B2 * | 10/2006 | Huff et al. | 607/116 |
| 7,174,211 B2 | 2/2007 | Spadgenske | |
| 7,539,542 B1 | 5/2009 | Malinowski | |
| 7,711,428 B2 | 5/2010 | Janzig et al. | |
| 7,736,192 B2 | 6/2010 | Alexander et al. | |
| 8,313,478 B2 | 11/2012 | Tockman et al. | |
| 8,401,673 B2 | 3/2013 | Bowe et al. | |
| 8,666,514 B2 * | 3/2014 | Tockman et al. | 607/122 |
| 2004/0230268 A1 | 11/2004 | Huff et al. | |
| 2004/0230269 A1 | 11/2004 | Huff et al. | |
| 2005/0033371 A1 | 2/2005 | Sommer et al. | |
| 2005/0177199 A1 | 8/2005 | Hansen et al. | |
| 2005/0222658 A1 * | 10/2005 | Hoegh et al. | 607/116 |
| 2006/0258193 A1 | 11/2006 | Hoecke et al. | |
| 2008/0015668 A1 * | 1/2008 | Soukup | 607/115 |
| 2008/0039900 A1 | 2/2008 | Stein et al. | |
| 2008/0082138 A1 | 4/2008 | Smits | |
| 2008/0177167 A1 * | 7/2008 | Janzig et al. | 600/373 |
| 2008/0208267 A1 | 8/2008 | Alexander et al. | |
| 2008/0248696 A1 | 10/2008 | Kast et al. | |
| 2011/0160824 A1 | 6/2011 | Ware et al. | |
| 2012/0019260 A1 | 1/2012 | Reddy et al. | |
| 2013/0001090 A1 * | 1/2013 | Rubinson et al. | 205/118 |

\* cited by examiner

PEEL-AWAY IS-4/DF-4 LEAD IMPLANT TOOL WITH ELECTRICAL CONTACTS

CROSS-REFERENCE TO RELATED APPLICATION

"This application is a continuation application of U.S. application Ser. No. 13/253,336. filed Oct. 5, 2011, now U.S. Pat. No. 8,666,514, which claims priority to U.S. Provisional Application 61/415,555, filed Nov. 19, 2010, both of which are herein incorporated by reference in their entireties."

TECHNICAL FIELD

The present invention generally relates to implantable medical devices. More particularly, the present invention relates to devices, systems and methods for installing and testing multi-conductor leads within a patient's body.

BACKGROUND

Various types of medical electrical leads for use in cardiac rhythm management (CRM) and neurostimulation applications are known. In CRM applications, for example, such leads are frequently delivered intravascularly to an implantation location on or within a patient's heart, typically under the aid of fluoroscopy. Once implanted, the lead is coupled to a pulse generator or other implantable device for sensing cardiac electrical activity, delivering therapeutic stimuli, and/or for performing some other desired function within the body. Such leads often include a distal electrode end which contacts the heart tissue, and a proximal, terminal end which is connected to the pulse generator. The distal electrode end of the lead typically includes one or more features such as an active fixation helix or a number of passive tines to facilitate securing the lead to the heart tissue. The terminal end of the lead, in turn, includes one or more electrical contacts that are electrically connected to the electrodes on the terminal end of the lead via a number of conductors.

In certain applications, the leads are tested for proper positioning and function as part of the implantation process and prior to being connected to the pulse generator, allowing the implanting physician to evaluate pacing and sensing performance prior to concluding that the particular lead position is suitable. During the resting process, for example, a Pacing System Analyzer (PSA) may be connected to the terminal end of the lead to evaluate the performance of the lead. To facilitate connection of the PSA to the lead, a lead implant tool can be temporarily coupled to the terminal end of the lead, allowing the conductors of the PSA to be connected to the electrical contacts on the terminal end of the lead. In some cases, for example, the implant tool may facilitate the attachment of several alligator cups, plunger dips, or other spring-loaded dips to the electrical contacts on the terminal end of the lead. Examples of lead implant tools for use in connecting the conductors of a PSA to a multi-conductor lead are described in U.S. Patent Publication No. 200510177199 to Hansen et al. and U.S. Patent Publication No. 2006/0258193 to Hoecke et al., each of which are incorporated herein by reference in their entirety for all purposes.

More recent trends in lead designs have focused on the development of lead connectors with up to four electrical contacts. The terminal end of such leads are not significantly different in size from previous, IS-1 standard leads, which include only two terminal contacts. Many existing spring-loaded dips used for connecting the PSA to the terminal contacts are often inadequate for use with more modern lead designs, particularly due to the limited spacing between the contacts, and since the space between the contacts is sometimes used as a sealing area to ensure electrical isolation.

SUMMARY

Example 1 is an implant tool for use with an implantable lead during an implant procedure including: a pliable sheath having an inner surface and an outer surface and comprising a proximal contact region and a distal gripping region, the pliable sheath defining a lumen extending from a proximal end through a distal end of the pliable sheath, the lumen sized to receive a terminal connector of an implantable lead therein; at least a first and a second electrical contact formed in the proximal contact region of the pliable sheath, the first and second electrical contacts extending from the outer surface to the inner surface of the pliable sheath and comprising an electrically conductive material; at least a first raised separation feature formed on the outer surface of the pliable sheath, the first raised separation feature disposed between the first and second electrical contacts.

In Example 2, the implant tool according to Example 1, wherein the raised separation feature extends about 360 degrees about outer circumference of the pliable sheath.

In Example 3, the implant tool according to any one of Examples 1 or 2, wherein the electrically conductive material comprises an electrically conductive polymer.

In Example 4, the implant tool according to any one of Examples 1-3, wherein the electrically conductive material comprises a polymer comprising electrically conductive particles dispersed therein.

In Example 5, the implant tool according to any one of Examples 1-4, wherein the electrically conductive material comprises a silicone rubber having a combination of silver and nickel particles dispersed therein.

In Example 6, the implant tool according to any one of Examples 1-5, wherein the electrically conductive material comprises a conductive metal foil.

In Example 7, the implant tool according to any one of Examples 1-6, wherein the gripping portion comprises at least one tab extending away from the pliable sheath and adapted to be gripped by a user to remove the pliable sheath from about a terminal connector of lead when in use.

In Example 8, the implant tool according to any one of Examples 1-7, wherein the pliable sheath further comprises a side slit formed in the wall of the pliable sheath, the slit extending from the proximal end to the distal end of the pliable sheath and having a width w that is adapted to be increased from a first width to a second width to facilitate attachment and/or removal of the pliable sheath.

In Example 9, the implant tool according to any one of Examples 1-8, wherein the pliable sheath further comprises at least one line of perforations or thin, frangible web extending from the proximal end to the distal end of the sheath.

In Example 10, the implant tool according to any one of Examples 1-9, wherein the pliable sheath further comprises at least one tear strip extending from the proximal end to the distal end of the pliable sheath.

In Example 11, the implant tool according to any one of Examples 1-10, wherein the pliable sheath further comprises a removable portion extending from the proximal end to the distal end of the pliable sheath.

Example 12 is a lead assembly including: an implantable medical electrical lead including a terminal connector adapted to be coupled to a pulse generator, the terminal connector comprising a terminal pin, a proximal ring electrode, a middle ring electrode and a distal ring electrode; and a lead implant tool disposed over the terminal connector, the lead implant tool comprising a pliable sheath having an inner surface and an outer surface and comprising a proximal contact region and a distal gripping region; at least a first and a second electrical contact formed in the proximal contact region of the pliable sheath, the first and second electrical contacts extending from the outer surface to the inner surface of the pliable sheath and comprising an electrically conductive material; and at least a first raised separation feature formed on the outer surface of the pliable sheath, the first raised separation feature disposed between the first and second electrical contacts.

In Example 13, the lead assembly according to Example 12, wherein the lead implant tool is disposed over the terminal connector such that the second electrical contact is aligned over the middle ring electrode of the terminal connector.

In Example 14, the lead assembly according to any one of Examples 12 or 13, wherein the first and second electrical contacts of the lead implant tool comprise a depression extending away from an inner surface of the implant tool in a direction towards the terminal connector over which the lead implant tool is disposed.

In Example 15, the lead assembly according to any one of Examples 12-14, wherein an inner diameter of the lead implant tool is slightly smaller than an outer diameter of the terminal connector.

In Example 16, the lead assembly according to any one of Examples 12-15, wherein the electrically conductive material forming the first and second electrical contacts of the implant tool comprises an electrically conductive polymer.

In Example 17, the lead assembly according to any one of Examples 12-16, wherein a width of the first and second electrical contacts is greater than a width of the corresponding ring electrode over which the first and second electrical contacts are disposed.

In Example 18, the lead assembly according to any one of Examples 12-17, wherein the lead implant tool is disposed over the terminal connector such that the terminal pin is exposed and accessible to a user.

In Example 19, the lead assembly according to any one of Examples 12-18, wherein the lead implant tool further comprises removal means for removing the lead implant tool from the terminal connector prior to connection of the terminal connector to a pulse generator.

In Example 20, the lead assembly according to any one of Examples 12-19, wherein the implant tool further comprises a roughened inner surface.

Example 21 is a method of using a lead implant tool for implanting and testing an implantable lead within a body. The lead implant tool includes: a pliable sheath having an inner surface and an outer surface and comprising a proximal contact region and a distal gripping region, the pliable sheath defining a lumen extending from a proximal end through a distal end of the pliable sheath, the lumen sized to receive a terminal connector of an implantable lead therein; at least a first and a second electrical contact formed in the proximal contact region of the pliable sheath, the first and second electrical contacts extending from the outer surface to the inner surface of the pliable sheath and comprising an electrically conductive material; at least a first raised separation feature formed on the outer surface of the pliable sheath, the first raised separation feature disposed between the first and second electrical contacts; and removal means for removing the lead implant tool from the terminal connector. The method includes the steps of: coupling a lead implant tool to a terminal connector located at a proximal end of an implantable lead; implanting a lead at a location within a patient's body; connecting a number of electrical connectors of a testing device to the lead implant tool; testing the lead implant tool; and peeling away the implant tool from the terminal connector using the removal means.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
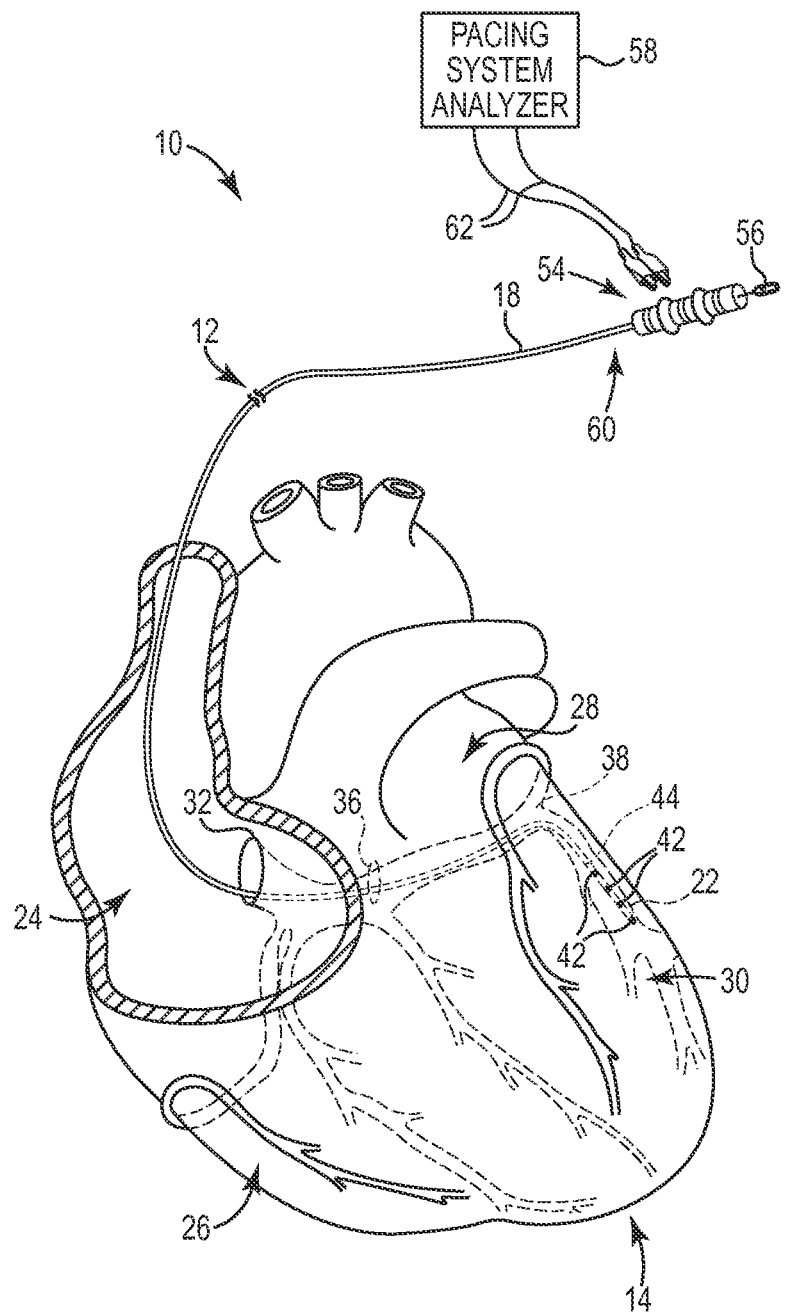
FIG. 1 is a schematic view showing an illustrative system for implanting and testing an implantable lead within the body of a patient.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view showing an illustrative system 10 for implanting and testing an implantable lead 12 within the body of a patient. For purposes of illustration and not limitation, the system 10 is described in conjunction with an implantable lead 12 for use in sensing cardiac electrical activity and/or for providing electrical stimulus therapy to a patient's heart 14. The system 10 can be used in other contexts where implantable leads are employed, and where testing is to be conducted prior to the connection of the lead to another implantable device such as a pulse generator. In certain embodiments, for example, the system 10 can be used to aid in the implantation and testing of an implantable neurostimulation lead prior to its connection to another implantable device such as a pulse generator.

According to various embodiments, the lead 12 includes a lead body 16 extending from a proximal end 18 adapted to be coupled to a pulse generator to a distal end 22. The lead 12 can be implanted in the patient's heart 14, which as shown in FIG. 1, includes a right atrium 24, a right ventricle 26, a left atrium 28, and a left ventricle 30. In the embodiment illustrated in FIG. 1, the distal end 22 of the lead 12 is transvenously guided through the right atrium 24, through the coronary sinus ostium 32, and into a branch of the coronary sinus 36 or great cardiac vein 38. The illustrated position of the lead 12 can be used for sensing or for delivering pacing energy to the left side of heart 14, or to treat arrhythmias or other cardiac disorders requiring therapy delivered to the left side of the heart 14. Additionally, in some embodiments, the lead 12 can be configured to provide treatment in other regions of the heart 14 (e.g., the right atrium 24 or right ventricle 26). The lead 12 can include one or more electrodes 42 for providing electrical therapy to and/or sensing therapy to the patient's heart 14. In certain embodiments, the implantable lead 12 is a quadripolar lead including four electrodes 42 located in a distal region 44 of the lead 12.

In the illustrative embodiment depicted, the system 10 further includes an implant tool 54, a stiffening member such as a stylet or guidewire 56, and a Pacing System Analyzer (PSA) 58 that can be used for implanting and testing the lead 12 within the body. During the course of the procedure, to evaluate the viability of a potential stimulation site, the function and location of the lead 12 can be tested by connecting a terminal connector 60 located at the proximal end 18 of the lead 12 to several electrical conductors 62 of the PSA 58. This evaluation can be performed after implantation of the lead 12 at the potential stimulation site. Such testing can be performed, for example, to verify that the electrodes 42 are properly positioned on or within the heart 14. The PSA 58 can also be used to perform other functions such as measuring pacing thresholds, lead impedance and r-wave amplitude.

The implant tool 54 can be used with passive fixation leads to enable stylet or guidewire passage and electrical connection while protecting the terminal connector 60. In other embodiments, other fixation mechanisms such as, for example, a fixation helix, can also be deployed via the implant tool 54. The implant tool 54 is configured to permit the implanting physician to easily feed various stylets or guidewires 56 into a pin lumen of the implantable lead 12, to make an electrical connection between the PSA conductors 62 and a terminal pin 64 (FIG. 2) and one or more terminal ring electrodes 66, 68, 70 (FIG. 2) on the lead 12.

In some embodiments, the implant tool 54 can be packaged and shipped already attached to an implantable lead 12. The pre-assembled components can then be packaged in a blister pack, pouch, or other suitable storage medium for later use by the implanting physician.

In use, the implant tool 54 protects the lead terminal connector 60 throughout the implant procedure from electrical clips or other surgical implements. As such, the implant tool 54 is configured such that it can remain coupled to the lead connector throughout the implantation and testing procedures, up to the point where the lead can be connected to another implantable device such as a pulse generator. At that time, the lead implant tool 54 is removed from the lead 12, and the lead 12 is then connected to the pulse generator. During normal operation, the lead 12 is configured to convey electrical signals back and forth between the pulse generator and the heart 14. For example, in those embodiments where the pulse generator is a pacemaker, the lead 12 can be used to deliver electrical therapeutic stimulus for pacing the heart 14. In those embodiments where the pulse generator is an implantable cardioverter defibrillator (ICD), the lead 12 can be utilized to deliver electric shocks to the heart 14 in response to an event such as a heart attack or ventricular tachycardia. In some embodiments, the pulse generator includes both pacing and defibrillation capabilities, or is capable of performing biventricular or other multi-site resynchronization therapies such as cardiac resynchronization therapy (CRT). Example leads and lead connectors that can be used in conjunction with the implant tool 54 can include, but are not limited to, pacing and CRT leads (e.g., including a quadripolar connector or IS-4 type connector), ICD leads (e.g., including a quadripolar, IS-4/DF-4 type connector), and pacing leads with sensing capabilities (e.g., a pressure sensing/pacing lead with a quadripolar type connector). Other types of leads and/or lead connector types can also be used in conjunction with the implant tool 54, as desired.

Figure 2:
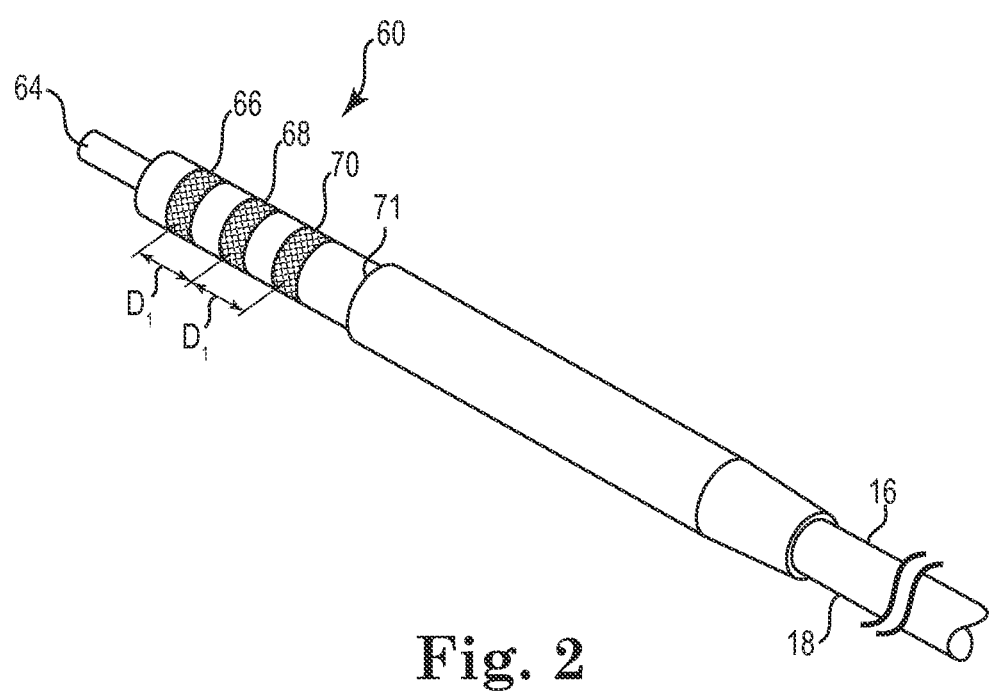
FIG. 2 is a perspective view showing the terminal end of the implantable lead of FIG. 1 in greater detail.

FIG. 2 is a perspective view showing the IS-4 terminal connector 60 of the implantable lead 12 of FIG. 1 in greater detail. As further shown in FIG. 2, the IS-4 terminal connector 60 includes a terminal pin 64 and a number of terminal rings 66, 68, 70 each spaced axially apart from each other at a distance $D_1$ along the length of the terminal connector 60. The terminal pin 64 is coupled to a first, distal most electrode 42 located in the distal region 44 of the lead 12 and serves as the cathode for the implantable lead 12. The first terminal ring 66 is electrically coupled to a second electrode 42, which can serve as a cathode or an anode for the implantable lead 12. The second and third terminal ring electrodes 68 and 70 are electrically coupled, respectively, to third and fourth electrodes located on a distal region 44 of the implantable lead 12.

Additionally, although the implantable lead 12 includes a terminal connector 60 having a terminal pin 64 and three terminal rings 66, 68, 70, in other embodiments the number and configuration of the terminal contacts may vary from that shown. In one embodiment, for example, the implantable lead 12 can comprise a bi-polar pacing lead including a terminal connector having a single terminal pin and ring electrode.

FIGS. 3A-3D are perspective views of the lead implant tool 54 according to various embodiments of the present invention. According to various embodiments, the implant tool 54 is provided over a terminal connector of an implantable medical lead such as, for example terminal connector 60 of FIG. 2. The implant tool 54 facilitates connection of variety of standard alligator clips to an implantable medical electrical lead in a safe, reliable manner that prevents the clips from shorting, and protects the terminal connector during testing and implantation of the lead. After testing and implantation of the lead is complete, the implant tool 54 can be easily removed from the terminal connector so that the lead can be connected to the pulse generator. In some embodiments, the implant tool 54 comes pre-mounted over the terminal connector of he lead such that when the physician removes he lead from its packaging from he manufacturer, the implant tool 54 is already in place and ready for use.

According to various embodiments of the present disclosure, as shown in FIGS. 3A-3D, the lead implant tool 54 is a light-weight, pliable polymer sheath 80. The pliable sheath 80 can be made from a variety of pliable polymers suitable for use in medical devices. The durometer of the polymer material used to form the pliable polymer sheath 80 is sufficiently low such that the pliable sheath 80 can conform to the terminal connector over which it is provided. Additionally, the durometer of the polymer material is sufficiently pliable such that the pliable polymer sheath 80 can be easily removed or peeled away from the terminal connector when the testing procedure and/or implantation of the lead is complete. In one non-limiting embodiment, the pliable sheath 80 is formed from 50 A-70 A durometer silicone.

The pliable polymer sheath 80 defines a lumen 84 extending from a proximal end 88 through a distal end 92 of the pliable sheath 80. The lumen 84 is sized and shaped to receive a terminal connector of an implantable lead therein. In one embodiment, an inner diameter d of the lumen 84 is slightly smaller than an outer diameter of the terminal connector such that compressive forces retain the implant tool 54 on the terminal connector.

Additionally, the polymer sheath 80 includes a proximal contact region 100 and a distal gripping region 104. At least two electrical contacts 108a, 108b are formed in the proximal contact region 100. In some embodiments, the proximal contact region 100 includes three electrical contacts, 108a, 108b and 108c. In other embodiments, the electrical contacts 108a-108c form pairs of diametrically opposed electrical contacts in the proximal contact region 100 of the pliable sheath 80.

The electrical contacts 108a, 108b and 108c extend from an outer surface 112 to an inner surface 116 of the pliable sheath 80. In some embodiments, the electrical contacts 108a-108c extend partially around an outer circumference 117 of the pliable sheath 80. For example, in one embodiment, each of the electrical contacts 108a-108c may extend in an arc ranging from about 60 degrees to about 180 degrees about the outer circumference 117 of the pliable sheath. In another embodiment, each of the electrical contacts 108a-108c may extend in an arc ranging from about 180 degrees to about 360 degrees about the outer circumference 117 of the pliable sheath 80. In still yet another embodiment, each of the electrical contacts 108a-108c may extend 360 degrees about the outer circumference 117 of the pliable sheath.

Figure 3A:
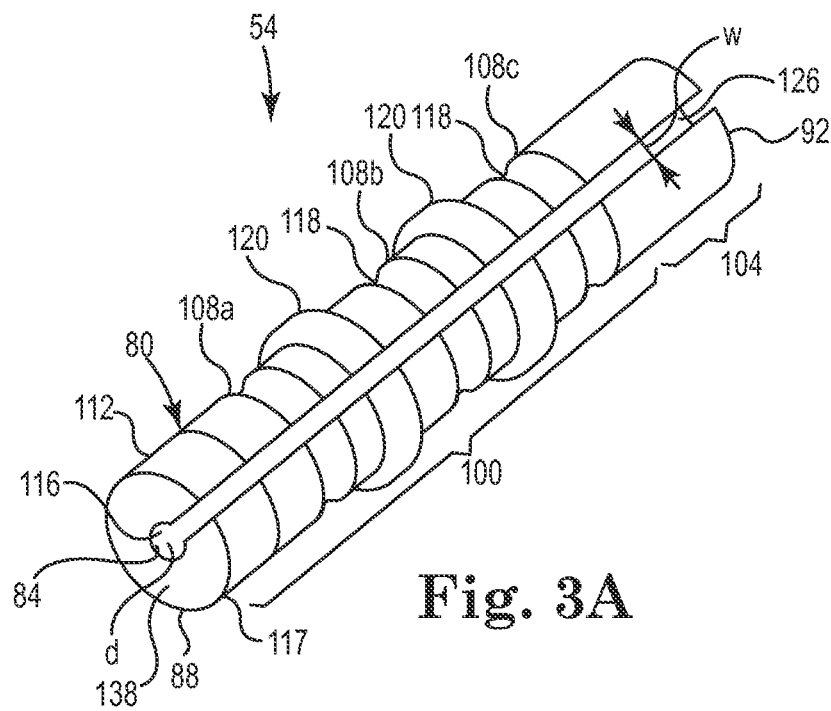
FIGS. 3A-3D are perspective views of a lead implant tool according to various embodiments of the present invention.
Figure 3B:
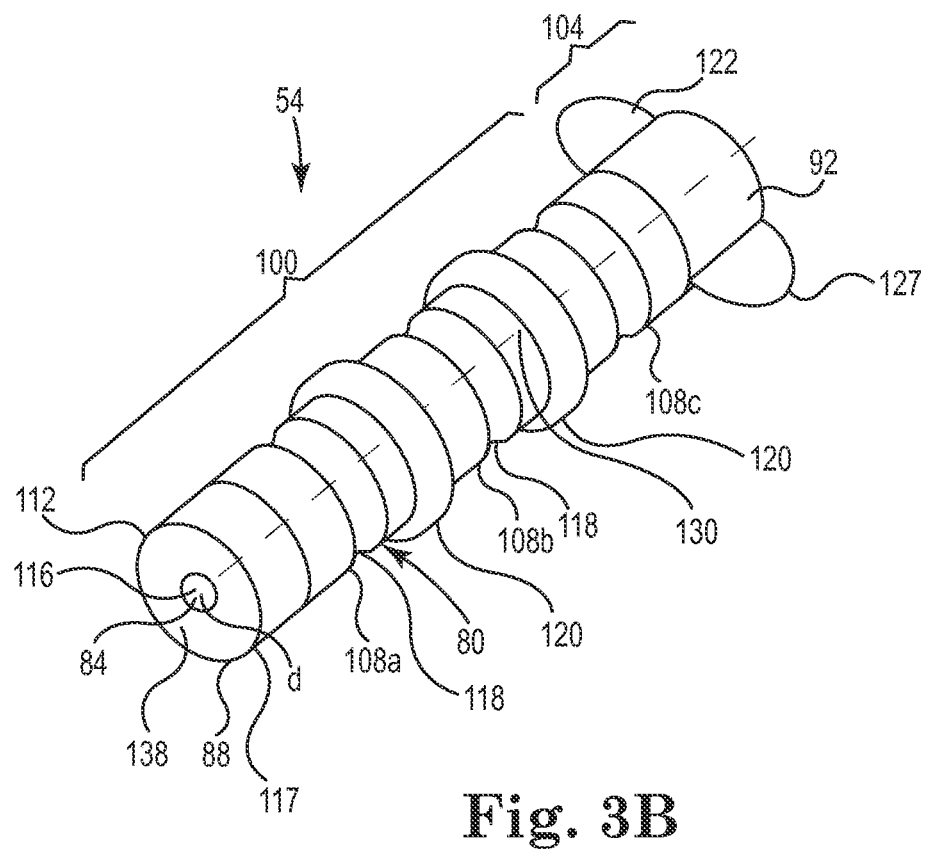
Figure 3C:
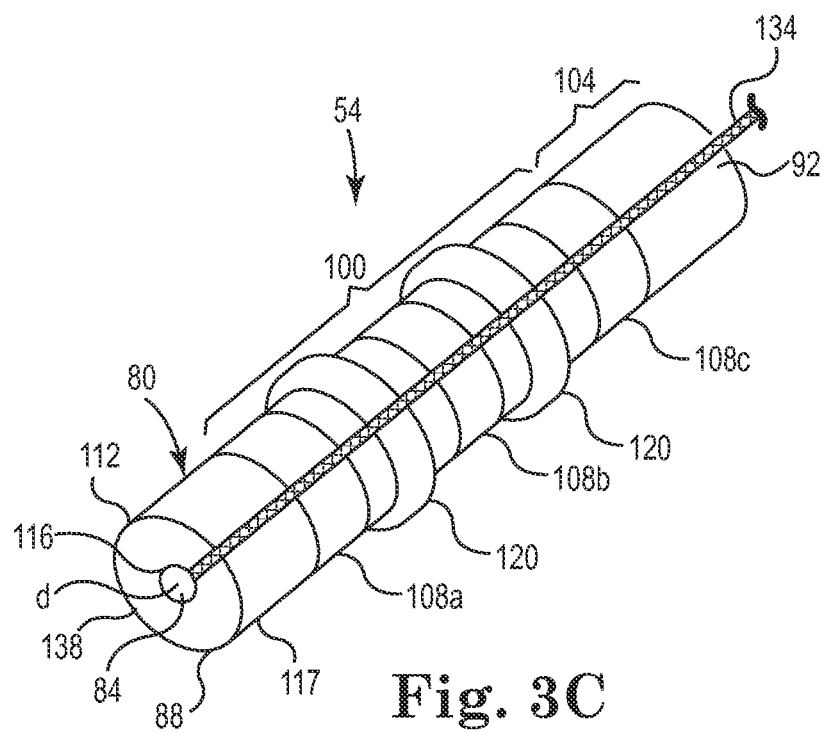
Figure 3D:
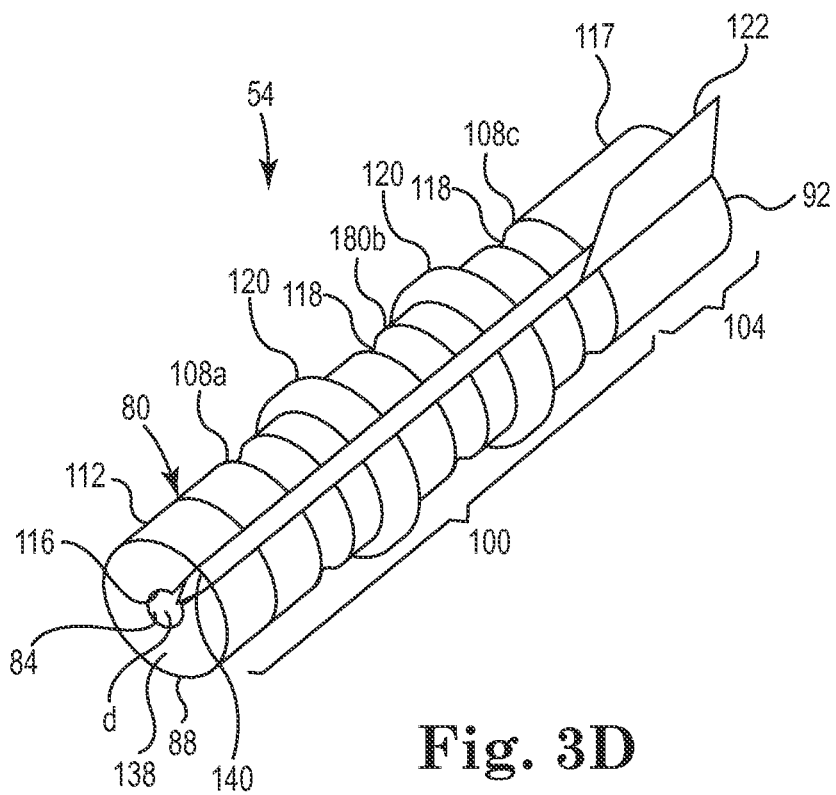

As shown in FIGS. 3A, 3B and 3D, the electrical contacts 108a-108c can also include a depression 118 to facilitate contact with the corresponding electrical contacts (e.g., the terminal rings 66, 68, 70) on the terminal connector 60. The depression 118 can be a bump, wedge or notch formed in the electrical contacts 108a-108c that extends away from the inner surface 116 of the sheath 80 and into the lumen 84. On the outer surface 112 of the sheath, the depression 118 may also serve as a guide for connection of the alligator dips to the terminal connector and may facilitate their retention.

In some embodiments, the electrical contacts 108a-108c are formed from a metal or metal ahoy foil. Suitable metals for forming the electrical contacts 108a-108c include, but are not limited to gold, silver, platinum, palladium, titanium, nickel, iridium and their respective alloys.

In other embodiments, the electrical contacts 108a-108c are formed from a conductor-filled polymer. Examples of conductor-filled polymers include polyurethanes, silicone elastomers, or other polymeric materials that are compounded with a conductive material. Suitable conductive materials include, but are not limited to carbon, graphite, grapheme, nickel, silver, gold and combinations thereof. The conductive material can be provided in the form of microparticles or nanoparticles, microfibers or nanofibers, microspheres or nanospheres and/or nanotubes. In one embodiment, the conductive material includes graphite nano-tubes. In another embodiment, the conductive material includes graphene. In still another embodiment, the conductive material includes a combination of silver and nickel spheres.

In still other embodiments, the electrical contacts 108a-108c can be formed from a conductive polymer. Intrinsically conductive polymers are conductive without requiring a non-polymeric conductive filler or coating, such as metallic compound or carbon. Intrinsically conductive polymers include alternating single and double bonds forming a conjugated backbone that displays electronic properties. Charge in intrinsically conductive polymers is transported along and between polymer molecules via charge carriers generated along the conjugated backbone. Intrinsically conductive polymers may include dopants to enhance their conductivity. Dopants may also help to control the conductivity characteristics of the polymer. The conductivity of intrinsically conductive polymers can generally range from semi-conducting to super conducting, depending upon the doping levels. Examples of intrinsically conductive polymers include, but are not limited to, the following: polypyrrole, polyacetylene, polythiophene, polyethylenedioxythiophene, poly (p-phenyl vinylene), polyaniline, polynapthalene, other suitable conductive polymers, and mixtures thereof.

Using a conductive polymer or a conductor-filled polymer such as, for example, a conductor-filled silicone maintains the overall pliability of the implant tool 54. Additionally, the conductive polymer material used to form the electrical contacts 108a-108c can be selected such that it is lower in durometer than the material used to form the remainder of the implant tool 54 such that the electrical contacts 108a-108c can be easily depressed to facilitate greater contact between the implant tool 54 and the electrodes on the terminal connector over which it is provided. In one embodiment, the electrical contacts 108a-108c are formed from a conductor-filled silicone such as, for example, NuSil Technology R-2637, available from NuSil Technology of Carpinteria, Calif.

In some embodiments, the inner surface 116 of the sheath 80 and the electrical contacts 108a-108c can be roughened. Roughening an inner surface of the electrical contacts 108a-108c may facilitate electrical contact between the electrical contacts 108-108c and their corresponding ring electrodes 66, 68 and 70 on the terminal connector 60. In one embodiment, the inner surface of the electrical contacts has an average surface roughness (Ra) ranging from about 20 micro-inches to about 50 micro-inches. Additionally, the inner surface 116 of the sheath 80 may also be roughened. Roughening the inner surface of the sheath 80 reduces the contact area between the inner surface 116 of the sheath 80 and the outer surface of the implant tool 54 and may facilitate removal of the sheath 80 from about the terminal connector 60. In some embodiments the average surface roughness (Ra) of the inner surface 116 of the sheath 80 ranges from about 40 micro-inches to about 50 micro-inches.

According to various embodiments, as shown in FIGS. 3A-3D, the proximal contact region 100 also includes at least one separation feature 120 disposed between adjacent electrical contacts or pairs of electrical contacts 108a-108c, such as electrical contacts 108a and 108b or electrical contacts 108b and 108c. In some embodiments, the separation feature 120 is a polymer ridge that extends away from the outer surface 112 and at least partially around an outer circumference 117 of the pliable sheath. In other embodiments, the separation feature 120 is a polymer ridge that extends away from the outer surface 112 and around the entire outer circumference 117 of the pliable sheath 80. The separation features 120 separate the electrical contacts 108a-108c from one another and prevent adjacent alligator dips from contacting one another when engaged with the implant tool 54. Additionally, the separation features 120 may serve as a visual guide for placement of the alligator dips in contact with the implant tool 54.

The implant tool 54 also includes removal means for facilitating removal of the tool 54 from about the terminal connector when testing and implantation of the lead is complete. According to some embodiments, the distal gripping region 104 can include one or more tabs or wings 122 (FIG. 3B) to facilitate removal of the implant tool 54 from the terminal connector when testing and implantation of the lead is complete. The wings or tabs 122 can be used in combination with other removal means such as a slit 126 (FIG. 3A), perforation line 130 (FIG. 3B), tear strip 134 (FIG. 3C) or removable section 140 (FIG. 3D) to remove or "peel away" the implant tool 54.

In some embodiments, as shown in FIG. 3A, the removal means includes a slit 126 formed in the side wall 138 of the pliable sheath 80. The slit 126 extends in a direction along the longitudinal axis of the sheath from the proximal end 88 to the distal end 92 of the sheath 80. The slit 126 has a width w that is adapted to be increased from a first width to a second width to facilitate installation and removal of the implant tool 54 over the terminal connector of a lead. The slit 126 can have any number of cross-sectional shapes. In one embodiment, the slit 126 can have a tapered profile.

In other embodiments, as shown in FIG. 3B, the removal means includes one or more perforation lines 130 formed in the side wall 138 of the pliable sheath 80. In other embodiments, the removal means includes one or more thin, frangible webs that facilitate removal of the sheath 80. The perforation lines 130 extend in a direction along the longitudinal axis of the sheath from the proximal end 88 to the distal end 92 of the sheath 80. The perforation lines 130 can be located 180 degrees from each other about the outer circumference 117 of the sheath 80 such that the sheath 80 can be split into two halves during the removal process. The individual perforations forming the perforation lines 130 can have any number of shapes useful for forming a perforation. In a further embodiment, as shown, the sheath 80 can also include one or more tabs 122 formed in the distal gripping region 104 of the sheath to facilitate removal of the sheath 80. The physician may pull on the tabs 122 to separate the sheath 80 at the perforation lines.

In still other embodiments, as shown in FIG. 3C, the removal means can include a tear strip 134. The tear strip 134 is provided in a side wall 138 of the pliable sheath 80 and extends from the proximal end 88 to the distal end 92 of the sheath 80. The tear strip 134 can be formed from a tougher material than the remainder of the pliable sheath. The physician can pull on the tear strip 134 leaving behind a slit in the sheath which then facilitates removal of the implant tool 54 from about the terminal connector. Alternatively, the tear strip 134 can include a small lumen that is slightly smaller than the wall thickness of the sheath 80 having a removable strip. Removal of the tear strip 134 including the small lumen will result in a very thin walled structure that can be separated by puffing the sides of the sheath 80 away from each other.

In still yet other embodiments, as shown in FIG. 3D, the removal means can include a removable section 140 that when removed leaves behind a slit in the side wall 138 of the sheath facilitating removal of the tool 54 from about the terminal connector. As shown in FIG. 3D, the removable section 140 can have a wedge-like shape and can be attached to a tab 122. Pulling on the tab 122 results in the removal of the removable section 140. The removable section 140 can be connected to the main portion of the sheath 80 by perforation lines or a thin, frangible web that facilitates easy separation of the removable section 140 from the sheath 80.

Figure 4A:
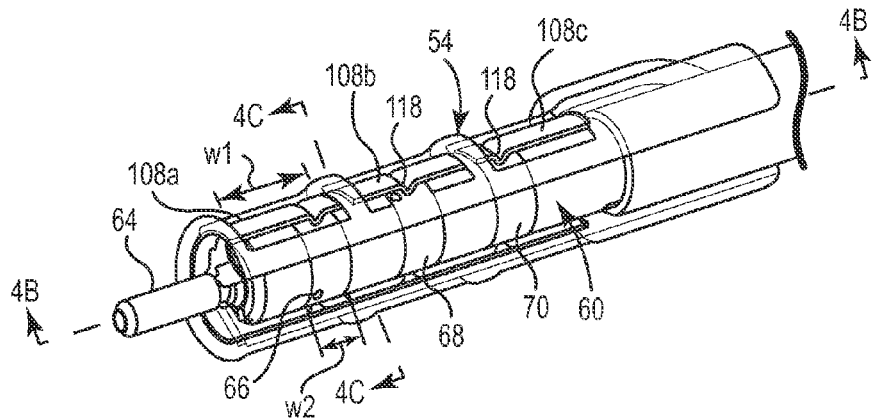
FIG. 4A is a diagrammatic view of a lead assembly including an implant tool provided over a terminal connector of a lead in accordance with an embodiment of the present invention.
Figure 4B:
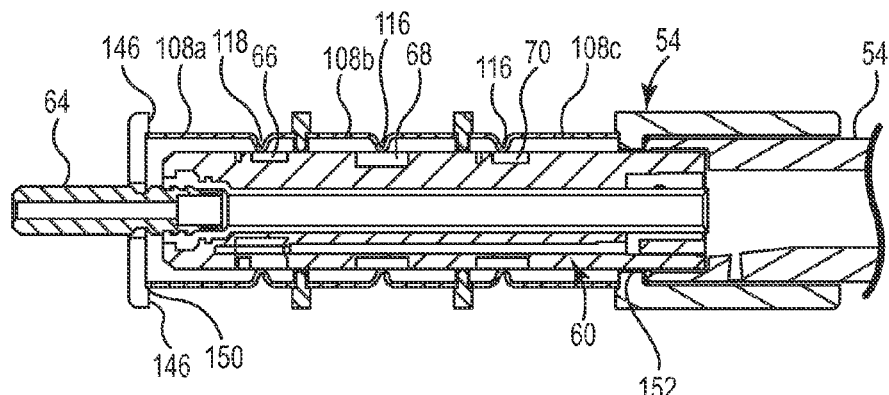
FIG. 4B is a longitudinal cross-sectional view taken along line 4B-4B of the implant tool and terminal connector shown in FIG. 4A.
Figure 4C:
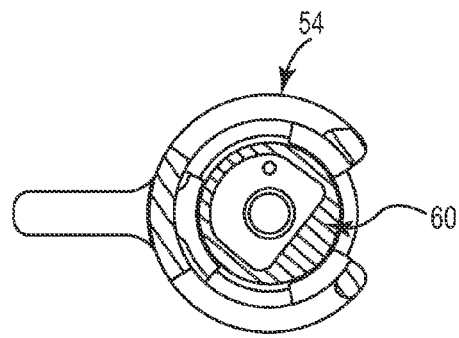
FIG. 4C is an end cross-sectional view taken along line 4C-4C of the implant tool and terminal connector shown in FIG. 4A.

FIGS. 4A-4C show various views of an implant tool 54 provided over the terminal connector 60 of an exemplary medical electrical lead 12. As shown in FIGS. 4A-4C, the implant tool 54 is provided over the terminal connector 60 such that the terminal pin 64 is exposed and accessible to a physician during the testing and implantation procedure. According to various embodiments, the implant tool 54 is positioned over the terminal connector 60 such that the middle electrical contact 108b is aligned with the middle electrode 68 on the terminal connector 60. The electrical contacts 108a-108c are spaced apart from one another such that alignment of the middle electrical contact 108b with the middle electrode 68 ensures proper positioning of the two remaining electrical contacts 108a and 108c relative to their corresponding electrodes 66 and 70 located on the terminal connector 60. If the implant tool 54 includes a slit or other similar feature, the position of the implant tool 54 relative to the terminal connector 60 can be visually confirmed after installation.

According to various embodiments, the implant tool 54 also includes an alignment feature to facilitate alignment of the electrical contacts 108a-c with the corresponding electrodes 66, 68 and 70 when the implant tool 54 is provided over the terminal connector 60 during the assembly process. For example in some embodiments, as shown in FIGS. 4A-4C, the pliable sheath 80 forming the implant tool 54 may include one or more stop features or shoulders formed on an inner surface 116 of the pliable sheath 80. In one embodiment, the pliable sheath 80 includes a proximal shoulder 146 adapted to abut the proximal end 150 of the terminal connector 60. In addition, the pliable sheath 80 can also include a distal shoulder 152 adapted to abut the implant tool 54.

In some embodiments, as shown in FIGS. 4A and 4B, the width w1 of each of the electrical contacts 108a-108c is greater than the width w2 of each of the ring electrodes 66, 68 and 70 of the terminal connector 60. Thus, the alligator clips need not be secured to the implant tool 54 directly over the electrodes. Rather, the difference in width between the electrical contacts 108a-108c of the implant tool 54 and the ring electrodes 66, 68 and 70, facilitate an increase in the spacing between adjacent alligator clips secured to the implant tool 54 while at the same time maintaining good electrical contact with the respective electrodes 66, 68, and 70 located on the terminal connector 60. Additionally, when the width w1 of each of the electrical contacts 108a-108c is greater that the width w2 of each of the ring electrodes 66, 68 and 70 of the terminal connector 60, the electrical contacts 108a-108c can accommodate a wide variety of alligator clips of varying sizes from different manufacturers.

Figure 5:
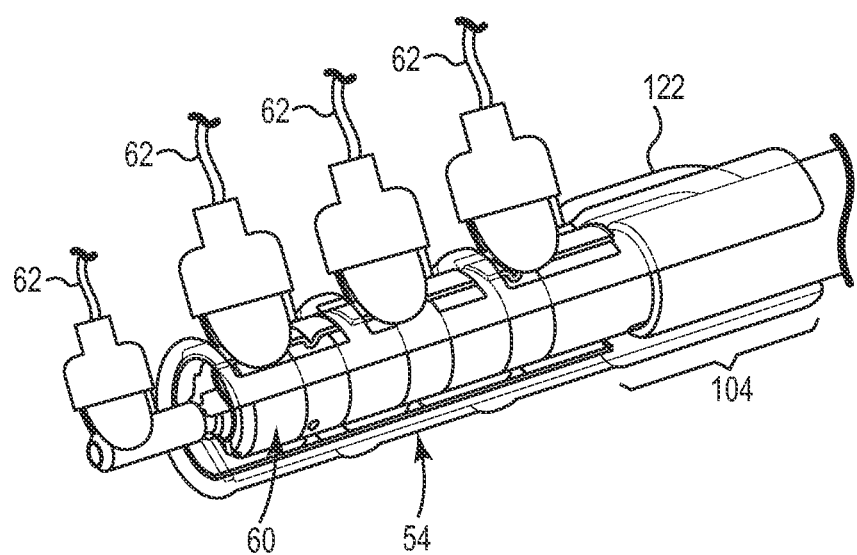
FIG. 5 is a schematic view showing a lead implant tool in use in accordance with an embodiment of the present invention.

FIG. 5 is a perspective view showing the lead implant tool 54 in use. In various embodiments, the lead implant tool 54 is pre-mounted over the terminal connector 60 of a lead such that when the lead is removed from its packaging, the lead implant tool 54 is already in place over the terminal connector 60. The physician guides the lead 12 through the patient's vasculature to one of many potential implant sites. To evaluate the viability of the potential implant site, the function and location of the lead can be tested by connecting the conductors 62 of a Pacing System Analyzer (PSA) to the lead implant tool 54 disposed over the terminal connector 60. The testing procedure is repeated each time the lead is repositioned until a suitable implant site is identified. The physician then completes the implantation procedure. After the implantation of the lead is complete, the physician removes the lead implant tool 54 from the terminal connector 60.

The implant tool 54 can be removed using one of the various removal means, described herein with reference to FIGS. 3A-3D according to the various embodiments of the present disclosure. In one embodiment, the physician grips a tab such as, for example, tab 122 provided in the gripping region 104 of the lead implant tool 54 and uses the tab 122 to remove or peel-away the implant tool 54 from the terminal connector 60. In another embodiment, the physician uses a first tab 122 to remove a section of the lead implant tool 54 leaving behind a slit. The physician then uses a second tab 122 provided on the gripping region 104 of the implant tool 54 to remove the tool 54 from the terminal connector 60. In yet another embodiment, the physician grips a pair of tabs 122 located 180 degrees opposite one another in the gripping region 104 of the terminal tool 54. The physician then uses these tabs 122 to separate the implant tool 54 into two halves along a line of perforation or weakness.

After the implant tool 54 has been removed from the terminal connector 60, the terminal connector is then engaged with the header of the PG.

Methods for forming the implant tool 54, described herein according to the various embodiments, will now be described.

In one embodiment, to form the implant tool 54 including the conductor-filled polymer contacts, a set of conductor-filled polymer rings is formed using a first shot mold having one or more cavities for forming the rings. Once molded and cured, the conductor-filled polymer rings can be placed over a core pin and into a second shot mold for overmolding of the non-conductive material portion of the implant tool 54. The second shot mold has the desired configuration of the implant tool 54. The conductor-filled polymer rings are placed over the core pin such that they have the desired spaced apart configuration. Non-conductive material is injected into the second shot mold, and the material cured. The finished implant tool 54 including the conductor filled polymer contacts is removed from the mold cavity and the core pin is removed.

In another embodiment, a conductor-filled polymer tube can be molded or extruded to the appropriate diameter and inner diameter. Additionally, the molded or extruded tube can be formed such that it includes features on the inner and/or outer diameter to facilitate cutting the tube into one or more segments. The tube is then cut into one or more segments of a desired length to form a number of conductor-filled polymer rings. The rings are then placed over a core pin such that they are spaced apart from one another at a desired distance. The core pin including the rings is then placed into a shot mold. The shot mold has the desired configuration of the implant tool 54. Non-conductive material is injected into the shot mold, and the material cured. The finished implant tool 54 including the conductor filled polymer contacts is removed from the mold cavity and the core pin is removed.

Similar methods to those described herein can be used to form an implant tool 54 including metallic foil electrical contacts. Primer can be added to the non-conductive material to facilitate adhesion between the non-conductive material and the metallic contacts. Also, in some embodiments, a stamping process can be used to form metallic rings.

Various modifications and additions can be made to the exemplary embodiments discussed without departing from the scope of the present invention. For example, while the embodiments described herein refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implant tool for use with an implantable lead during an implant procedure, the implant tool comprising:
    a pliable sheath having an inner surface and an outer surface and comprising a proximal contact region and a distal gripping region, the pliable sheath defining a lumen extending from a proximal end through a distal end of the pliable sheath, the lumen sized to receive a terminal connector of an implantable lead therein;
    at least a first and a second electrical contact formed in the proximal contact region of the pliable sheath, the first and second electrical contacts extending from the outer surface to the inner surface of the pliable sheath and comprising an electrically conductive material; and
    at least a first separation feature being disposed between the first and second electrical contacts and extending radially inwardly from the inner surface of the pliable sheath such that the first separation feature is configured to be capable of contacting an outer surface of the terminal connector;
    wherein the pliable sheath is configured to be peeled away from the terminal connector.

2. The implant tool according to claim 1, wherein the first and second electrical contacts extend radially inwardly from the inner surface of the pliable sheath and are configured to be capable of contacting the outer surface of the terminal connector.

3. The implant tool according to claim 2, wherein the first and second electrical contacts are configured to be capable of contacting electrical contact portions of the terminal connector.

4. The implant tool according to claim 1, wherein the first separation feature extends radially inwardly from the inner surface of the pliable sheath such that the first separation feature is capable of contacting a portion of the outer surface of the terminal connector adjacent to an electrical contact of the terminal connector.

5. The implant tool according to claim 1, wherein the first separation feature extends radially inwardly from the inner surface of the pliable sheath such that the first separation feature is capable of contacting a portion of the outer surface of the terminal connector that is formed of a non-conductive, polymeric material.

6. The implant tool according to claim 1, wherein the first separation feature extends radially inwardly over a first radial distance and the first electrical contact extends radially inwardly over a second radial distance from the inner surface of the pliable sheath, wherein the first and second radial distances are substantially equivalent.

7. The implant tool according to claim 1, wherein the first separation feature is configured between the first and second electrical contacts such that the first separation feature minimizes electrical shorting during the implant procedure.

8. The implant tool according to claim 1, wherein the first separation feature is configured to contact the outer surface of the terminal connector.

9. The implant tool according to claim 1, wherein the first separation feature extends approximately 360 degrees about an outer circumference of the terminal connector.

10. The implant tool according to claim 1, wherein the first separation feature extends about at least a portion of an outer circumference of the terminal connector.

11. A lead assembly comprising:
    an implantable medical electrical lead including a terminal connector adapted to be coupled to a pulse generator, the terminal connector comprising a terminal pin, a proximal ring electrode, a middle ring electrode and a distal ring electrode; and
    a lead implant tool disposed over the terminal connector, the lead implant tool comprising a pliable sheath having an inner surface and an outer surface and comprising a proximal contact region and a distal gripping region; at least a first and a second electrical contact formed in the proximal contact region of the pliable sheath, the first and second electrical contacts extending from the outer surface to the inner surface of the pliable sheath and comprising an electrically conductive material; and at least a first separation feature formed on the inner surface of the pliable sheath, the first separation feature being disposed between the first and second electrical contacts;

wherein the pliable sheath is configured to be peeled away from the terminal Connector.

12. The implant tool according to claim 11, wherein the first separation feature extends radially inward of the inner surface of the pliable sheath such that the first separation feature is capable of contacting a portion of the outer surface of the terminal connector.

13. The implant tool according to claim 11, wherein the first separation feature is further formed on the outer surface of the pliable sheath.

14. The implant tool according to claim 13, wherein the first separation feature extends about 360 degrees about an outer circumference of the pliable sheath.

15. The implant tool according to claim 11, wherein the pliable sheath is configured to contact the outer surface of the terminal connector such portions of the pliable sheath conform to the outer surface of the terminal connector.

16. A method of using a lead implant tool for implanting and testing an implantable lead within a body, the method comprising:

coupling a lead implant tool to a terminal connector located at a proximal end of an implantable lead, the lead implant tool comprising:

a pliable sheath having an inner surface and an outer surface and comprising a proximal contact region and a distal gripping region, the pliable sheath defining a lumen extending from a proximal end through a distal end of the pliable sheath, the lumen sized to receive the terminal connector of an implantable lead therein;

at least a first and a second electrical contact formed in the proximal contact region of the pliable sheath, the first and second electrical contacts extending from the outer surface to the inner surface of the pliable sheath and comprising an electrically conductive material;

at least a first separation feature formed on the inner surface of the pliable sheath and extending radially inwardly from the inner surface of the pliable sheath, the first separation feature being disposed between the first and second electrical contacts;

and removal means for removing the lead implant tool from the terminal connector;

implanting a lead at a location within a patient's body;

connecting a number of electrical connectors of a testing device to the lead implant tool;

testing the lead implant tool; and peeling away the lead implant tool from the terminal connector using the removal means.

17. The method according to claim 16, wherein coupling the lead implant tool to the terminal connector further includes disposing the lead implant tool over the terminal connector such that the first electrical contact come into contact with the electrical contacts of the terminal connector.

18. The method according to claim 16, wherein coupling the lead implant tool to the terminal connector further includes disposing the lead implant tool over the terminal connector such that the first separation feature contacts the outer surface of the terminal connector.

19. The method according to claim 16, wherein coupling the lead implant tool to the terminal connector further includes disposing the lead implant tool over the terminal connector such that the first separation feature contacts a portion of the outer surface of the terminal connector that is formed of a non-conductive, polymeric material.

20. The method according to claim 16, wherein coupling the lead implant tool to the terminal connector further includes disposing the lead implant tool over the terminal connector such that portions of the pliable sheath conform to the outer surface of the terminal connector.

* * * * *